United States Patent [19]

Holden et al.

[11] Patent Number: 5,484,603
[45] Date of Patent: Jan. 16, 1996

[54] PERCUTANEOUS ANAESTHESIA

[75] Inventors: Paul Holden, York; Barry M. Sandbank, Chester, both of United Kingdom

[73] Assignee: Smith & Nephew plc, United Kingdom

[21] Appl. No.: 119,070

[22] PCT Filed: Mar. 20, 1992

[86] PCT No.: PCT/GB92/00518

§ 371 Date: Nov. 12, 1993

§ 102(e) Date: Nov. 12, 1993

[87] PCT Pub. No.: WO92/16202

PCT Pub. Date: Oct. 1, 1992

[30] Foreign Application Priority Data

Mar. 21, 1991 [GB] United Kingdom .................... 9105977

[51] Int. Cl.⁶ .................................................. A61F 13/00
[52] U.S. Cl. ........................ 424/447; 424/449; 514/817
[58] Field of Search ................................. 424/448, 447, 424/449; 514/817

[56] References Cited

U.S. PATENT DOCUMENTS

| | | | |
|---|---|---|---|
| 4,562,060 | 12/1985 | Broberg | 424/28 |
| 4,899,739 | 2/1990 | Konishi | 128/156 |
| 4,904,475 | 2/1990 | Gale | 424/449 |
| 4,951,657 | 8/1990 | Pfister | 128/156 |

FOREIGN PATENT DOCUMENTS

| | | |
|---|---|---|
| 0250125 | 12/1987 | European Pat. Off. . |
| 0331392 | 9/1989 | European Pat. Off. . |
| 8809169 | 12/1988 | WIPO . |

*Primary Examiner*—J. Gabrielle Phelan
*Attorney, Agent, or Firm*—Roseman & Colin

[57] ABSTRACT

A percutaneous anaesthetic delivery system comprises a skin conformable backing layer, an amethocaine-bearing material and a layer having little or no tendency to absorb amethocaine intermediate the backing layer and the layer of amethocaine bearing material which may be in the form of a film, mat or net.

15 Claims, 1 Drawing Sheet

PERCUTANEOUS ANAESTHESIA

This application is a 371 of PCT/GB92/00518 filed Mar. 20, 1992.

This invention relates to the administration of percutaneous local anaesthetics and more particularly to delivery systems for the topical administration of amethocaine.

In UK Patent Specification No. 1108837, there is proposed a film-forming composition comprising a copolymer of vinyl acetate and crotonic acid having, for example, amethocaine (2-dimethylaminoethyl p-butyl aminobenzoate) intimately dispersed therethrough. Such compositions are intended for use on mucous membranes and are activated by the action of saliva, for example, which dissolves the film-forming polymer and liberates the anaesthetic agent.

Such compositions cannot readily be employed for local percutaneous anaesthesia where it is highly desirable that both the area of the administration site be strictly controlled and the minimum quantities of anaesthetic are used to provide an effective unit dose.

It is desirable that the anaesthetic containing material can be applied readily and retained on the skin at the place of use. It is also highly desirable that the materials be highly conformable.

Although it has been proposed to laminate or cover the local anaesthetic containing polymer film with water insoluble, water resistant or water impermeable backing material there have been no proposals to concentrate the amethocaine at the skin contacting surface of the delivery system. We have found that amethocaine has a tendency to migrate towards and, possibly, into the backing layer. Thus in order to provide effective anaesthetic amounts at the point of use, considerably larger quantities than those required for a unit dose have to be incorporated into the film forming polymer. Thus controlled administration may be difficult to achieve and time taken for effective anaesthesia maybe impossible to determine in advance.

We have now found that effective anaesthesia may be obtained reproducibly and in a minimum amount of time by use of a highly conformable dressing-type applicator system wherein the amethocaine is concentrated and retained in the skin-contacting region of the delivery system.

BRIEF DESCRIPTION OF THE DRAWINGS

The anaesthetic delivery system is more clearly described in the following discussion and drawings in which.

Figure 1:
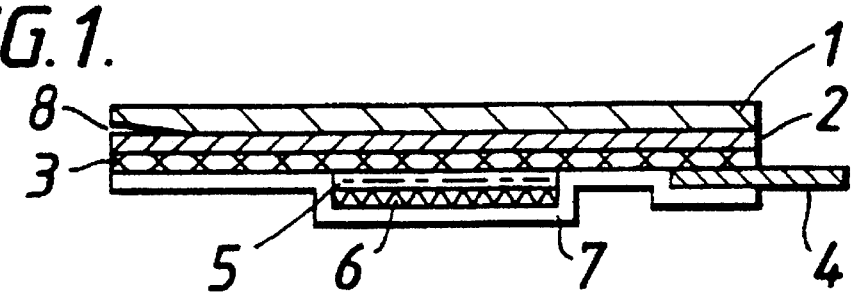
FIG. 1 is a cross section of a dressing in accordance with the present invention.

In accordance with the present invention there is provided a percutaneous anaesthetic delivery system comprising a skin conformable backing layer, an amethocaine-bearing material and a layer having little or no tendency to absorb amethocaine intermediate the backing layer and the layer of amethocaine bearing material.

The amethocaine-bearing material maybe a water-soluble or water-dispersible film forming material having amethocaine intimately mixed and distributed therethrough. The amethocaine loading in the film-forming material preferably should be as high as possible, aptly at least 10% by weight, more aptly at least 40% by weight of the material. Suitably, it will be at least 50%, and most suitably from 60 to 80% by weight. The amount of amethocaine present in the dressing should, aptly be sufficient to deliver at least 0.3 mg cm$^{-2}$ to the skin.

The film forming polymer may be any pharmaceutically acceptable water-soluble material which does not adversely react with or affect the amethocaine. Suitable materials include highly water-soluble polymers such as polyvinylpyrrolidone, carbomers such as those sold under the trade name CARBOPOL, polyvinylpyrrolidone-vinyl acetate copolymers and cellulose derivatives such as hydroxy propyl cellulose, for example those sold under the trade name KLUCEL.

A preferred example of the amethocaine-bearing material is polyvinylpyrrolidone film, having a film weight of about 17 gm m$^{-2}$ and wherein the ratio of amethocaine to polyvinylpyrrolidone is about 64:36. Under certain circumstances, for example, where the carrier material for the amethocaine has desirable properties, eg. adhesive properties, it may be advantageous to adjust the ratio of film forming polymer to maximise these properties. For example, where polyvinylpyrrolidone is used as the film forming polymer, it is possible to employ formulations which require no additional adhesive to attach the system to the skin. Systems eg. in the form of patches may therefore be cut to a desired size.

In an alternative embodiment, the amethocaine-bearing layer may be in the form of a net or fibrous matt composed of water soluble, water dispersible or water insoluble materials. Although the amethocaine may be incorporated into the fabric of these materials it is preferred that the amethocaine, as a free base, is coated onto the surface of the strands or fibres comprising the net or matt.

Suitable fibrous materials include films or sheets having a fibrous surface, nets and porous fabrics.

Suitable films or sheets having a fibrous surface include films or sheets with an integral pile surface. Such as those disclosed in U.S. Pat. No. 3967683.

Preferred fibrous materials are porous fabrics. Suitably porous fabrics for use in the invention include knitted, woven, non-woven and net fabrics. Preferably the fabrics comprise small fibres to obtain a good bond between the solid anaesthetic and the fabric.

Favoured porous fabrics are non-woven fabrics and fibrous net fabrics.

Preferably the fibrous materials comprises a polymer which does not absorb substantial amounts of the anaesthetic.

Suitable polymers include textile fibre polymers such as polyolefines for example polypropylene, polyethylene blends thereof with other polymers, polyamide or polyester.

Highly suitable porous fabrics include the non-woven fabrics and nets as used cover layers on sanitary towels and like absorbent products. Such fabrics are conformable fabrics which have a weight per unit area of 2 to 30 g/m$^2$ and comprise textile fibre polymers of the type herein above mentioned.

Favoured non-woven fabrics comprise spun bonded or heat bonded fibres. Apt non-woven fabrics include non-woven fabrics of spun bonded polyamide known as Cerex available from James River Corp. and heat bonded polypropylene coated polyester non-woven fabrics known as Finntex and in particular grade F10 made by Fibre-Filter Oy. Cerex and Finntex F10 have a weight per unit area of 10 g/m$^2$ and 8 g/m$^2$ respectively.

Favoured nets for use in the invention are fibrous nets. Suitable nets of this type are disclosed in United Kingdom Patent Nos. 1548865, 1531715 and 1055963.

Such nets can comprise an incompatible blend of polymers. Suitable blends comprise a major proportion of a polyolefine such as polypropylene, high density polyethylene or ethylene-propylene copolymers and a minor proportion of an incompatible polymer such as polystyrene, for example high impact polystyrene or polyamide. Preferred nets for use in the invention comprise a blend of high density polyethylene and 5 to 20% by weight of high impact polystyrene. Such nets have weight per unit area of 2 to 20 g/m$^2$.

Apt nets of this type are known as net 909, type X650S, DH120 H8, A7 or DHM available from Smith & Nephew Plastics Ltd.

The structure of the film, net or fibrous material should allow the layer of solid anaesthetic to be confined mainly on its skin contacting surface.

The intermediate layer should be formed from a material which has substantially little or no affinity for amethocaine. This material is aptly in the form of a conformable film. Suitably it may be a self-supporting film or a film which is supported either by the backing layer or by the amethocaine bearing layer.

The affinity of the material of the intermediate layer for amethocaine is a function of the rate at which amethocaine will diffuse into the material and the degree to which amethocaine is soluble in the material. It is preferred that the material exhibits a very low rate of diffusion and, more preferably, also will solubilise amethocaine either very sparingly or most preferably not at all.

Diffusion or flux through the intermediate layer will also depend to a greater or lesser extent upon the thickness of the layer. Thus thick materials having a relatively high amethocaine diffusion coefficient may have the required lack of affinity for amethocaine because the solubility for amethocaine is low but may not be useful because they are too thick to be conformable. Suitable materials for use in the intermediate layer of the invention have an amethocaine permeability ie. flux normalised to a thickness of 25 μm, of less than 50 μgm cm$^{-2}$ hr$^{-1}$. More suitably the layer will have a permeability of less than 10 μg cm$^{-2}$ 25 μm$^{-1}$ hr$^{-1}$. Most preferably the material will exhibit no detectable flux and very little or no solubility for amethocaine.

Aptly the intermediate layer is a water-insoluble material such as a suitable plastics film for example a metallised polyester film or a water soluble material such as a film of a water soluble grade of polyvinyl alcohol. Other materials suitable for use as the barrier layer include non-metallised polyester films, silicone rubbers and metallised and non-metallised grades of polypropylenes and polyethylenes. As used herein the term polyethylene includes linear low density polyethylenes, low density polyethylenes and high-density polyethylenes. Metal foils may also be employed for the barrier layer provided that their thickness is sufficiently low enough to prevent permanent creasing.

The thickness of the intermediate layer should be sufficiently great to prevent passage of amethocaine into the backing and yet thin enough as not to adversely affect the conformity of the dressing.

Examples of preferred water insensitive material exhibiting no detectable flux and being readily conformable are polyisobutadiene, aptly at a thickness of upto 100 μm, eg. about 26 μm; ethylene-vinyl acetate copolymer films, having a thickness aptly upto 100 μm, for example about 47 μm; polyethylene, for example having a thickness of 30 μm, polyethylene terephthalate film (sold under the trade name MELINEX), aptly having a thickness of upto 50 μm, for example about 23 μm and aluminium foil aptly having a thickness of upto 50 μm for example 14 μm.

Polyvinyl alcohol films having coating weights of 10 to 20 gm m$^{-2}$ have been found to be suitable. Although thicker polyvinyl alcohol films for example upto 200 gm m$^{-2}$ can be utilised a greater volume of water is required to plasticise this layer to render it conformable.

The backing layer of the system of the invention preferably should comprise a highly conformable sheet like material such as a thin film. The backing layer may advantageously extend beyond the area of the amethocaine and/or intermediate layer. Suitably the backing layer may also comprise an adhesive, aptly a pressure sensitive adhesive, coating to secure the backing layer to the remaining system components and, where the backing extends beyond the edges of the intermediate and amethocaine bearing layers, to secure the applicator to the skin.

The backing or supporting layers employed in the present invention should be capable of conforming to the body contours when applied to the skin and should be flexible enough to move with the body without becoming detached. Suitable flexible backing materials include knitted, woven or non-woven fabrics, nets, microporous films such as plasticised polyvinyl chloride films, polymer blend films containing voids, polymeric films, including thermoplastic polyurethane and hydrophilic polyurethane, elastomeric polyesters, styrene-butadiene block copolymers such as Kraton (Trade Mark) thermoplastic rubbers. Such hydrophilic polyurethanes will be those which will contain at least 5% by weight water when hydrated.

Suitable hydrophilic polyurethanes include those having the composition and prepared by the process described in British Patent No. 2093190B. The most suitable hydrophilic polyurethanes are those which contain from 5 to 50% by weight of water when hydrated more suitably to 10 to 40% by weight of water and which have a thickness when present in a dressing of from 25 to 1250 μm, more suitably 30 to 60 μm. A preferred film of hydrophilic polyurethane has a water content when hydrated of 20 to 30% for example 25% and a thickness of 50 μm for example 30 μm.

A favoured flexible backing material is a microporous plasticised polyvinyl chloride film formed by the process disclosed in British Patent No. 884232. The preferred microporous plasticised polyvinyl chloride 30 to films have a thickness of from 100 to 300 μm, for example 150 μm, 200 μm and 250 μm.

A further favoured backing layer is a thermoplastic polyurethane including the linear polyester polyurethanes or polyether polyurethanes known as Estanes (Trade Mark). Such polyurethanes are used as films from 15 to 75 μm in thickness, more favourably 20 to 35 μm in thickness for example about 25 μm or 30 μm.

Suitable backing materials formed from polymer blends containing voids include blends coating polyurethane and polybutadiene as the continuous phase and hydrocarbon such as high impact polystyrene as the disperse phrase.

It is preferred that the delivery system of the present invention be conformable so that it readily conforms to the contours of the human skin. The anaesthetic applicators of the present invention are suitable for use in anaesthetising venous puncture sites, such as in the crook of the arm, minor surgery and skin grafts as well as useful paediatric uses. In such cases it is highly desirable that the system be adhered to the skin and that it readily conforms to the skin movement in order that effective local anaesthesia may be induced in the minimum time.

At temperatures below about 42° C. the amethocaine base is present as a solid. When hydrated the melting point is depressed to about 32° C. Thus amethocaine may be made available for penetration through the skin by wetting the amethocaine bearing material at ambient temperatures. Wetting dissolves the polymer and liberates free amethocaine which is then hydrated and at skin temperature is available as a mobile oily liquid which is rapidly absorbed by the skin.

Activating the amethocaine layer may be achieved by either wetting the layer directly or by wetting the skin and applying it to the dampened skin.

In an alternative embodiment, the amethocaine may be present in the layer as a salt such as the hydrochloride. The amethocaine is activated by applying a suitable base, preferably as an aqueous solution to the amethocaine salt-containing layer to generate and hydrate the free base. Suitable bases include sodium borate (borax) for example as 2% solution and aqueous solutions of sodium dihydrogen phosphate.

In addition to the backing, intermediate and amethocaine bearing layers the system may be provided with additional means to facilitate handling and application. For example with systems which are highly conformably or otherwise difficult to handle, a carrier layer maybe provided on the surface of the backing layer opposed to the intermediate layer. This layer may be temporarily secured to the backing layer and can be removed once the system is in place.

If the system has a skin contacting adhesive surface it may be desirable to provide protection sheets over these surfaces. The protectors may also extend over the amethocaine bearing layer. In use the protector sheets are removed prior to adhering the system to the skin.

The system of the invention may be provided in the form of individual dressings or in a continuous strip or roll form to be cut to the desired shape and size.

The systems of the inventions are activated either by wetting with water or aqueous base or by applying the system to dampened skin. Where the systems are activated by wetting, depending on the construction, the amethocaine bearing layer may be contacted with the aqueous medium or its skin-contacting surface or by wetting from the opposed surface through the other layers.

Figure 2:
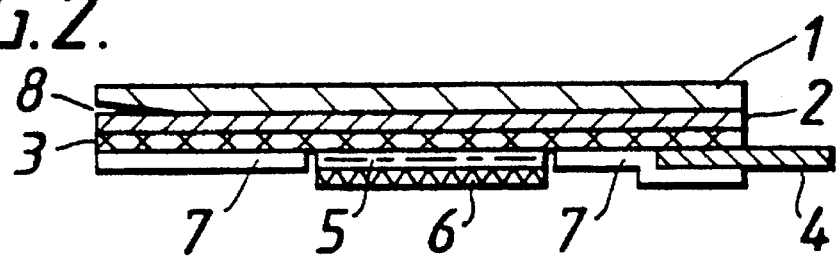
FIG. 2 is a cross section of the dressing of FIG. 1, provided with an aperture in the skin contacting layer.
Figure 3:
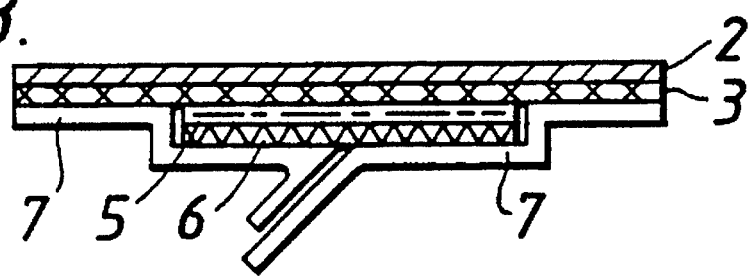
FIG. 3 is a cross section of the dressing of FIGS. 1 and 2, without the carrier layer and with a two part self removable protector sheet.

Referring to FIGS. 1 to 3, a dressing comprises a flexible carrier sheet 1, cast on to a layer of polyurethane to form a backing sheet 2. The backing sheet 2 is provided with an adhesive layer 3 and an amethocaine layer 6, with an amethocaine phobic layer 5, intermediate the amethocaine layer 6 and the adhesive layer 3. In addition, the dressing is provided with a protector layer 7 overlying the amethocaine layer 6, the adhesive layer 3, and a non-adhesive tab 4, intermediate the adhesive layer 3 and the protector layer, in order to facilitate removal of the protector layer 7.

With reference to FIG. 2, the protector layer 7 is apertured and the carrier sheet 1 is provided with a nick 8 to facilitate removal of said carrier sheet 1.

With reference to FIG. 3, the protector layer 7 is provided in two parts.

Figure 4:
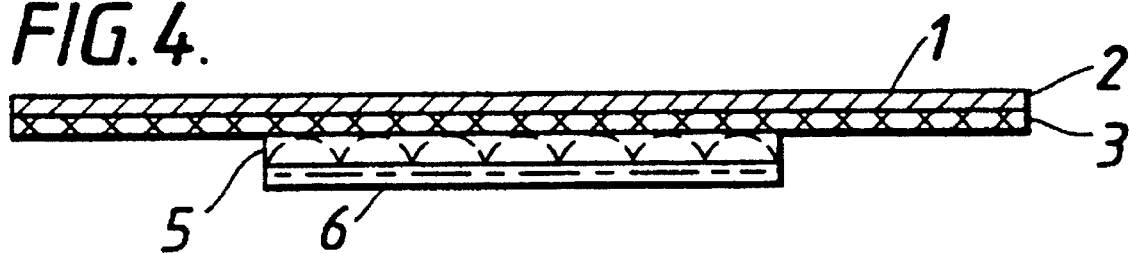
FIG. 4 is a cross section of a dressing of the present invention wherein the intermediate layer is a coverstock layer.
Figure 5:
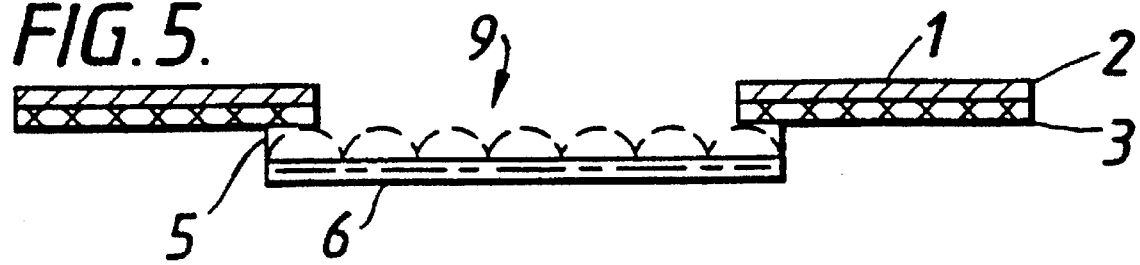
FIG. 5 is a cross section modification of dressing of FIG. 4, wherein the backing layer is apertured.

With reference to FIGS. 4 and 5, the intermediate layer 5 may comprise a coverstock and, optionally, a portion of the backing layer 2 and the adhesive layer 3 may be apertured, such that the aperture 9 registers with the major parts of the area of the intermediate layer 5 or coverstock.

The invention will be further described and illustrated by the following examples and by reference to the accompanying drawings which are schematic elevated views of systems in accordance with the invention.

EXAMPLE 1

A dressing as shown in FIG. 1 was produced in the following manner.

Onto a flexible polypropylene carrier sheet 1 was cast a layer of polyurethane 2. Layer 2 forms the backing. An acrylic adhesive as described in UK Patent No. 2070631 was coated onto the polypropylene/polyurethane composition to form layer 3. A non-adhesive tab 4 was applied to one edge of the adhesive layer 3.

A 12.5 cm wide strip of polyvinyl alcohol was cast (at a weight of 30 gm m$^{-2}$) onto a siliconised release paper and allowed to dry. A blend of amethocaine (8.8% w/w) and polyvinyl pyrrolidone (10% w/w) in isopropyl alcohol was spread through a spreading block having a gap set at 15.25 μm to a width of 9.0 cm on the dried polyvinyl alcohol strip and allowed to dry. The dried amethocaine containing layer comprised 64% w/w amethocaine and 34% w/w polyvinyl pyrrolidone.

Samples of the laminate measuring 3.0×4.5 cm were cut out and after removal of the release paper applied centrally to layer 3. The polyvinyl alcohol layer formed the intermediate layer 5 whilst the amethocaine/polyvinyl pyrrolidone layer formed the skin contacting layer 6.

A protection sheet 7 was laid onto the amethocaine bearing material and adhesive surfaces, covering both surfaces.

In use, an area of skin is first moistened. The protection sheet is then removed and the applicator applied to skin in the crook of the elbow, holding the applicator by tab 4. Once the applicator is adhered to the skin the carrier sheet 1 is lifted at the edge relieved portion 8 and removed from the applicator.

In a test after 30 minutes the applicator was removed from the skin, and the area under the dressing was found to be fully anaesthetised.

EXAMPLE 2

A dressing as shown in FIG. 2 was produced. This was produced in a similar manner to that described in Example 1 except that the protector layer was apertured in the region of layer 6.

In use layer 6 was wetted with water before the protector layer 7 was removed. Thus the areas of skin to which the adhesive was applied were kept dry.

EXAMPLE 3

A dressing was produced in accordance with the manner described in Example 1.

Thus a solution consisting of 8.8% w/w and 10% w/w polyvinyl pyrrolidone in isopropyl alcohol (qs-100% w/w) was spread through a spreading block gap of 15.25 μm (6 thousandths of an inch) onto a metallised polyester sheet to form a strip 9 cm wide, air dried for 3 hours and dried for a further 0.5 hour at a temperature of 50° C.

The metallised polyester film was 12 μm thick and 18 cm wide and supported on a flat surface prior to casting amethocaine of the polyvinyl pyrrolidone blend form a strip 9 cm wide. The cast strip comprised 66% w/w amethocaine and 34% w/w vinyl pyrrolidone. 3×4.5 cm samples of the coated film were cut out and applied centrally to the adhesive layer three.

After a protection sheet 7 was laid over the amethocaine bearing layer 6 and the peripheral adhesive are 3, the strip was cut up to form individual dressings 6.5 cm wide with the amethocaine layer being 3 cm wide by 4.5 cm long.

EXAMPLE 4

A dressing as shown in FIG. 2 was produced. This was produced in a similar manner to that described in Example 2 except that the protector layer was apertured in the region of layer 6.

In use layer 6 was wetted with water before the protector layer 7 was removed. Thus the areas of skin to which the adhesive was applied were kept dry.

EXAMPLE 5

An anaesthetic patch was prepared as shown in FIG. 4 by taking a filmic layer 2 of Estane coated with an adhesive layer 3 as described in Example 1.

A mixture 6 of polyvinyl pyrrolidone and amethocaine (36/64) was coated onto and embossed apertured coverstock material 5 for example as described in GB-A-2188278.

The two parts of the patch are then brought together.

In use the patch is hydrated by application of water to the PVP/amethocaine composition prior to application to the patch to the skin.

In a modification of the above delivery system as shown in FIG. 5, a hole 9 is punched in the composite layers 2,3 prior to bringing together of the two composite parts 2,3 and 5,6.

The coated coverstock 5,6 and adhesive coated backing 2,3 were brought together such that the hole in backing registered with a major part of the area of the coverstock 5.

In use the patch is applied to dry skin and the patch hydrated by the application of water through the hole 9.

EXAMPLE 6

A number of dressings were prepared according to Example 1 (Dressing A), Example 3 (Dressing B) and a placebo (Dressing C) which was prepared in accordance with Example 1 except that the polyvinyl pyrrolidone layer did not contain any amethocaine.

Each of 15 blind folded volunteers had two dressings of each type to the back of the hand, the inner forearm or the antecubital fossa (the crook of the elbow). After 45 minutes the blind folds and dressings were removed and the volunteers requested to record any sensation to pain resulting from a self-inflicted pin prick challenge consisting of 9 individual pin pricks across the entire area of the site previously covered by the dressing. The volunteers had to record that the prick was either painful or completely painless (for a site to be completely painless there had to be no experience of pain at all of the nine locations). The challenges were performed hourly for six hours.

With Dressing Type A 80% of the volunteers reported complete anaesthesia after 45 minutes and all reported anaesthesia after two hours. Anaesthetic lasted for at least three hours and 50% reported complete anaesthesia after the six hour challenge. Results using Dressing B were similar except that at the six hour challenge only a third of the volunteers were reporting complete anaesthesia. No cases of anaesthesia were reported using the placebo.

We claim:

1. A percutaneous anaesthetic delivery system comprising a skin conformable backing layer, an amethocaine-bearing material comprising at least 10% by weight of amethocaine and a layer having little or no tendency to absorb amethocaine intermediate the backing layer and the layer of amethocaine bearing material; wherein the amethocaine bearing material comprises a film, net or fibrous mat and wherein the amethocaine in the amethocaine bearing layer is present in the surface of said layer which is adapted to be in direct contact with the skin during use.

2. A system according to claim 1 wherein the intermediate layer has an amethocaine flux of less than 10 μg cm$^{-2}$ 25 μm$^{-1}$ hr$^{-1}$.

3. A system according to claim 1 wherein the intermediate layer comprises a polymeric film.

4. A system according to claim 3 wherein the film is a water insoluble film.

5. A system according to claim 3 wherein the film is a metallised film.

6. A system according to claim 1 wherein the intermediate layer is a water soluble material.

7. A system according to claim 1 wherein the amethocaine-bearing layer comprises a mixture of amethocaine free base and a water-soluble or water dispersible polymer.

8. A system according to claim 1 wherein the backing layer extends beyond the area of the intermediate or amethocaine-bearing layer.

9. A system according to claim 1 wherein the backing layer also comprises an adhesive layer.

10. A system according to claim 1 wherein the backing layer comprises knitted, woven fibres, non-woven fibres, nets, microporous polymer films or continuous polymer films.

11. A system according to claim 1 wherein the amethocaine is present as the free base.

12. A system according to claim 1 wherein the amethocaine is present as a acid salt.

13. A system according to claim 1 wherein the amethocaine is dispersed within a film forming medium to form an amethocaine bearing layer comprising at least 40% by weight amethocaine.

14. A method for inducing topical anaesthesia which comprises moistening the amethocaine bearing layer of a dressing as defined in claim 1 and applying to a body area.

15. A method according to claim 14 wherein the amethocaine bearing layer is applied to wetted skin.

* * * * *